US012778498B2

(12) United States Patent
Viswanath et al.

(10) Patent No.: US 12,778,498 B2
(45) Date of Patent: Nov. 3, 2026

(54) RADIOMICS SIGNATURES FOR PATHOLOGIC CHARACTERIZATION OF STRICTURES ON MR AND CT ENTEROGRAPHY

(71) Applicants: Case Western Reserve University, Cleveland, OH (US); The Cleveland Clinic Foundation, Cleveland, OH (US)

(72) Inventors: Satish E. Viswanath, Beachwood, OH (US); Florian Rieder, Shaker Heights, OH (US); Prathyush Chirra, Cleveland, OH (US); Joseph Sleiman, Pittsburgh, PA (US); Namita Sharma Gandhi, Chagrin Falls, OH (US); Ilyssa Gordon, Beachwood, OH (US)

(73) Assignees: Case Western Reserve Univerity, Cleveland, OH (US); The Cleveland Clinic Foundation, Cleveland, OH (US)

( * ) Notice: Subject to any disclaimer, the term of this patent is extended or adjusted under 35 U.S.C. 154(b) by 841 days.

(21) Appl. No.: 17/971,065

(22) Filed: Oct. 21, 2022

(65) Prior Publication Data

US 2024/0130673 A1 Apr. 25, 2024
US 2024/0225536 A9 Jul. 11, 2024

(51) Int. Cl.
*G06K 9/00* (2022.01)
*A61B 5/00* (2006.01)
(Continued)

(52) U.S. Cl.
CPC .......... *A61B 5/4842* (2013.01); *A61B 5/4255* (2013.01); *A61B 5/7264* (2013.01);
(Continued)

(58) Field of Classification Search
CPC ... A61B 5/4842; A61B 5/4255; A61B 5/7264; G06V 10/44; G06T 7/0012; G06T 7/40;
(Continued)

(56) References Cited

U.S. PATENT DOCUMENTS 12,053,316 B2 * 8/2024 Antoniades ............ A61B 6/032
2011/0082188 A1 * 4/2011 Chakravarti ............. A61P 1/00
435/7.1

(Continued)

OTHER PUBLICATIONS

Li, Xuehua, et al. "Development and validation of a novel computed-tomography enterography radiomic approach for characterization of intestinal fibrosis in Crohn's disease." Gastroenterology 160.7 (2021): 2303-2316. (Year: 2016).*

(Continued)

*Primary Examiner* — Avinash Yentrapati
(74) *Attorney, Agent, or Firm* — Eschweiler & Potashnik, LLC

(57) ABSTRACT

The present disclosure, in some embodiments, relates to a non-transitory computer-readable medium storing computer-executable instructions that, when executed, cause a processor to perform operations, including accessing an imaging data set having one or more radiological images of a patient having Crohn's disease, the one or more radiological images including one or more intestinal strictures; identifying a plurality of determinative features from within the one or more intestinal strictures in the one or more radiological images, the plurality of determinative features being associated with one or more pathological features used to identify inflammation or fibrosis within an intestinal stricture; and applying a machine learning model to the plurality of determinative features to identify an extent of inflammation or fibrosis within the one or more intestinal strictures.

20 Claims, 11 Drawing Sheets

(51) Int. Cl.
*G06T 7/00* (2017.01)
*G06T 7/40* (2017.01)
*G06V 10/44* (2022.01)

(52) U.S. Cl.
CPC .............. *G06T 7/0012* (2013.01); *G06T 7/40* (2013.01); *G06V 10/44* (2022.01); *G06T 2207/10081* (2013.01); *G06T 2207/10088* (2013.01); *G06T 2207/20081* (2013.01); *G06T 2207/30028* (2013.01)

(58) Field of Classification Search
CPC . G06T 2207/10081; G06T 2207/10088; G06T 2207/20081; G06T 2207/30028
See application file for complete search history.

(56) References Cited

U.S. PATENT DOCUMENTS

| | | | | |
|---|---|---|---|---|
| 2014/0205541 | A1* | 7/2014 | James | A61B 5/055 424/9.3 |
| 2015/0141800 | A1* | 5/2015 | Linguraru | A61B 5/055 600/410 |
| 2019/0249221 | A1* | 8/2019 | Rodriguez-Palacios | C12Q 1/28 |
| 2020/0270344 | A1* | 8/2020 | Bebbington | A61P 37/00 |
| 2022/0110598 | A1* | 4/2022 | Antoniades | A61B 6/032 |
| 2022/0233151 | A1* | 7/2022 | Shelton, IV | A61B 5/11 |
| 2023/0117179 | A1* | 4/2023 | Jule | G06T 7/0012 382/129 |

OTHER PUBLICATIONS

Kalpathy-Cramer, Jayashree, et al. "Radiomics of lung nodules: a multi-institutional study of robustness and agreement of quantitative imaging features." Tomography 2.4 (2016): 430. (Year: 2016).*
Gordon, Ilyssa O., et al. "International consensus to standardise histopathological scoring for small bowel strictures in Crohn's disease." Gut 71.3 (2022): 479-486. (Year: 2022).*
Li, Xuehua, et al. "Development and validation of a novel computed-tomography enterography radiomic approach for characterization of intestinal fibrosis in Crohn's disease." Gastroenterology 160.7 (2021): 2303-2316. (Year: 2021).*

* cited by examiner

RADIOMICS SIGNATURES FOR PATHOLOGIC CHARACTERIZATION OF STRICTURES ON MR AND CT ENTEROGRAPHY

FEDERAL FUNDING NOTICE

This invention was made with government support under CA248226 awarded by the National Institutes of Health and W81XWH-21-1-0345 awarded by the Department of Defense. The government has certain rights in the invention.

BACKGROUND

Crohn's disease is a chronic inflammatory bowel disease (IBD) that affects the lining of the digestive tract. Over time, it can cause swelling of digest tract tissue, which can lead to symptoms such as abdominal pain, diarrhea, fatigue, weight loss, and malnutrition.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
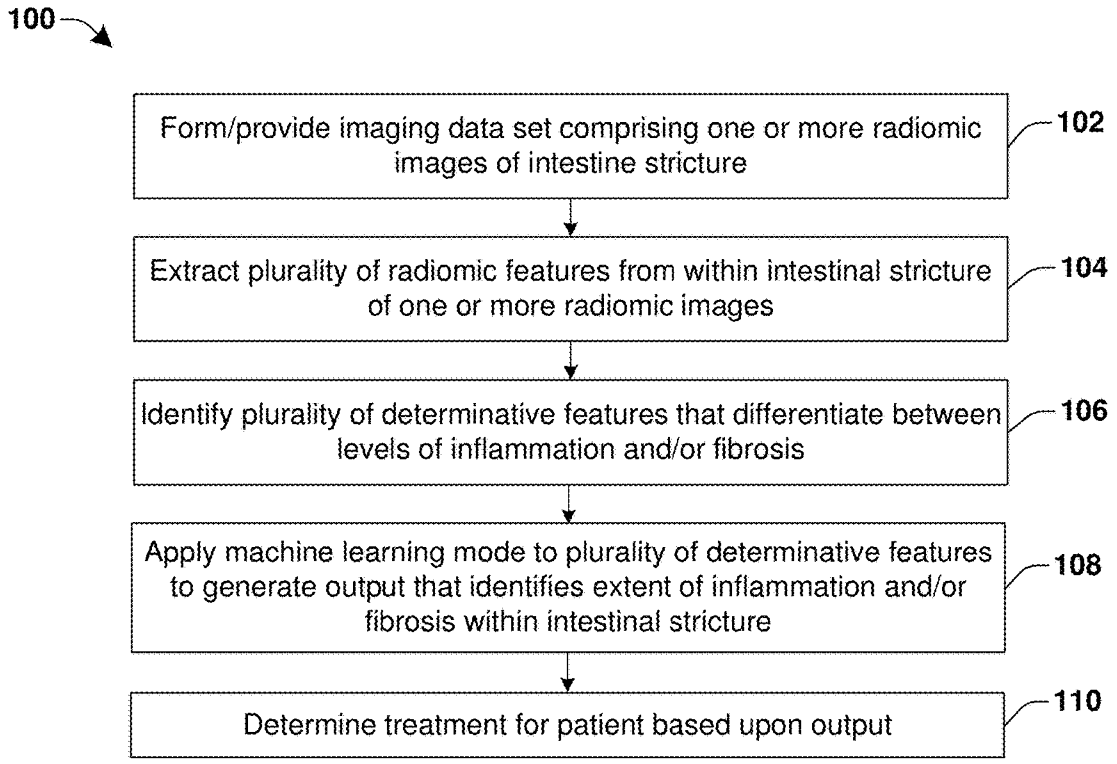
FIG. 1 illustrates a flow diagram showing some embodiments of a method of assessing an extent of inflammation and/or fibrosis within intestinal strictures.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Crohn's disease is a chronic inflammatory bowel disease, which over time may result in intestinal strictures. An intestinal stricture is an area of narrowing in a patient's gastrointestinal tract (e.g., intestines). During a cycle of inflammation and healing, scar tissue can replace normal cells in the lining of the intestines. After repeated cycles, scar tissue may build up along walls of an intestine resulting in narrowing of the intestine. Occasionally, this narrowing can get so severe that it can cause bowel obstruction. Twenty-five percent of patients with Crohn's disease develop severe intestinal strictures which are non-responsive to standard-of-care medication. In part, this is because intestinal strictures from Crohn's disease are complex and originate from both inflammatory and non-inflammatory pathways that involve fibrosis and smooth muscle hyperplasia.

Current non-invasive cross-sectional imaging modalities cannot accurately determine an extent of fibrotic and/or inflammatory components within an intestinal stricture. For example, cross-sectional imaging techniques, such as magnetic resonance enterography (MRE) and CT enterography (CTE), have emerged as accurate methods for diagnosing intestinal strictures and assessing their obstructing and penetrating complications. However, such imaging techniques cannot distinguish between inflammatory and fibrotic components of an intestinal stricture. It has been appreciated that early and non-invasive determination of an extent of inflammation and/or fibrosis within an intestinal stricture could facilitate the selection of targeted therapy or earlier surgical resection to improve patient outcomes.

Therefore, the present disclosure relates to a non-invasive method that applies a machine learning model to radiomic features extracted from radiological images (e.g., MRE images and/or CTE images) to assess an extent of inflammation and/or fibrosis within intestinal strictures. In some embodiments, the method comprises forming and/or providing an imaging data set comprising one or more radiological images including an intestinal stricture. A plurality of radiomic features are extracted from within the intestinal stricture in the one or more radiological images. The plurality of radiomic features are provided to a machine learning model that is configured to utilize the plurality of radiomic features to determine an extent of inflammation and/or fibrosis within the intestinal stricture. Determining an extent of inflammation and/or fibrosis within an intestinal stricture gives a health care professional information that enables them to make an earlier and/or more informed decision regarding treatment options (e.g., to use either anti-inflammatory therapy, endoscopic therapies, or surgical resection), thereby improving patient outcomes.

FIG. 1 illustrates a flow diagram 100 showing some embodiments of a method of assessing an extent of inflammation and/or fibrosis within intestinal strictures.

At act 102, an imaging data set is formed and/or provided to comprise one or more radiological images of intestinal strictures. In some embodiments, the one or more radiological images may comprise magnetic resonance enterography (MRE) images of one or more patients having Crohn's disease. In other embodiments, the one or more radiological images may comprise computed tomography enterography (CTE) images of one or more patients having Crohn's disease.

At act 104, a plurality of radiomic features are extracted from within an intestinal stricture of the one or more radiological images. In various embodiments, the plurality of radiomic features may comprise texture features, morphological features, and/or the like.

At act 106, a plurality of determinative features are identified from the plurality of radiomic features. The plurality of determinative features are a subset of the plurality of radiomic features that differentiate between different levels of inflammation and/or fibrosis. For example, in some embodiments the plurality of determinative features may differentiate between severe inflammation and minimal inflammation. In other embodiments, the plurality of determinative features may differentiate between severe fibrosis and minimal fibrosis.

At act 108, the plurality of determinative features are acted upon by a machine learning model (e.g., a machine learning classifier) that is configured to utilize the plurality of determinative features to generate an output that identifies an extent of inflammation and/or fibrosis within the intestinal stricture.

At act 110, a treatment plan for a patient may be determined based upon the output of the machine learning model. Because the output of the machine learning model allows for a health care professional to assess an extent of inflammation and/or fibrosis within the intestinal stricture, the output can enable the health care professional to make a more informed decision regarding treatment options and thereby provide for better treatment of the patient.

Figure 2:
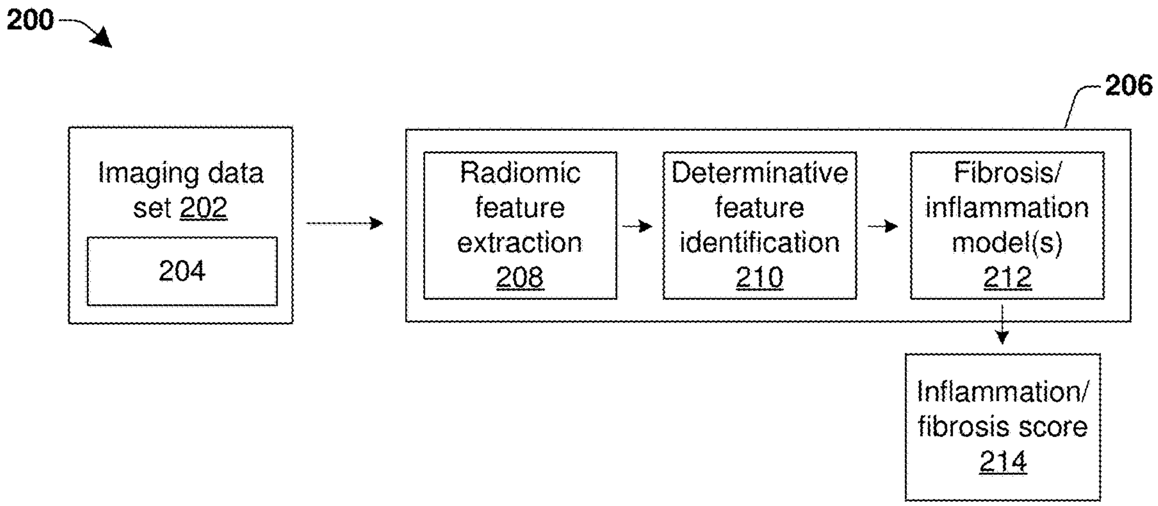
FIG. 2 illustrates some embodiments of a block diagram of a machine learning pipeline configured to assess an extent of inflammation and/or fibrosis within intestinal strictures.

FIG. 2 illustrates some embodiments of a block diagram 200 of a machine learning pipeline configured to assess an extent of inflammation and/or fibrosis within intestinal strictures.

As shown in the block diagram 200, an imaging data set 202 is formed and/or provided. The imaging data set 202 comprises one or more radiological images 204 of one or more patients having Crohn's disease. The one or more radiological images 204 respectively comprise one or more intestinal strictures. In some embodiments, the intestinal strictures may comprise ileal strictures and/or ileocecal valve strictures.

The one or more radiological images 204 are provided to a machine learning pipeline 206. The machine learning pipeline 206 comprises a plurality of machine learning stages 208-212 that are configured to extract radiomic features from the one or more radiological images 204 and to utilize the extracted radiomic features to determine an extent of inflammation and/or fibrosis within an intestinal stricture. In some embodiments, the machine learning pipeline 206 comprises a radiomic feature extraction stage 208, a determinative feature identification stage 210, and an inflammation and fibrosis model stage 212.

The radiomic feature extraction stage 208 is configured to extract a plurality of radiomic features from an intestinal stricture within the one or more radiological images 204. In some embodiments, the plurality of radiomic features may comprise texture features and/or morphological features (e.g., describing a shape, size, or the like) associated with the intestinal stricture.

The determinative feature identification stage 210 is configured to identify a plurality of determinative features that are most determinative (e.g., important) to identify fibrosis and/or inflammation within the intestinal stricture. In some embodiments, the determinative feature identification stage 210 may identify a plurality of fibrosis features that are most important to determine an extent of fibrosis within the intestinal stricture. In some embodiments, the determinative feature identification stage 210 may identify a plurality of inflammation features that are most important to determine an extent of inflammation within the intestinal stricture.

The inflammation and fibrosis model stage 212 is configured to apply and/or generate one or more machine learning models that utilize the plurality of determinative features to determine an extent of inflammation and/or fibrosis within the intestinal stricture. In some embodiments, the inflammation and fibrosis model stage 212 may be configured to generate an inflammation score and/or a fibrosis score. The inflammation score is a first numeric values that is indicative of an extent of (e.g., a percentage of) inflammation within the intestinal stricture. The fibrosis score is a second numeric values that is indicative of an extent of (e.g., a percentage of) fibrosis within the intestinal stricture.

In various embodiments, the one or more machine learning models within the inflammation and fibrosis model stage 212 may comprise a linear classifier. For example, in some embodiments the one or more machine learning models may comprise a support vector machine (SVM) classification method. In other embodiments, the one or more machine learning models may utilize a linear discriminant analysis (LDA) classification method, a quadratic discriminant analysis (QDA) classification method, a Naive Bayes classification method, or the like.

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device.

Figure 3:
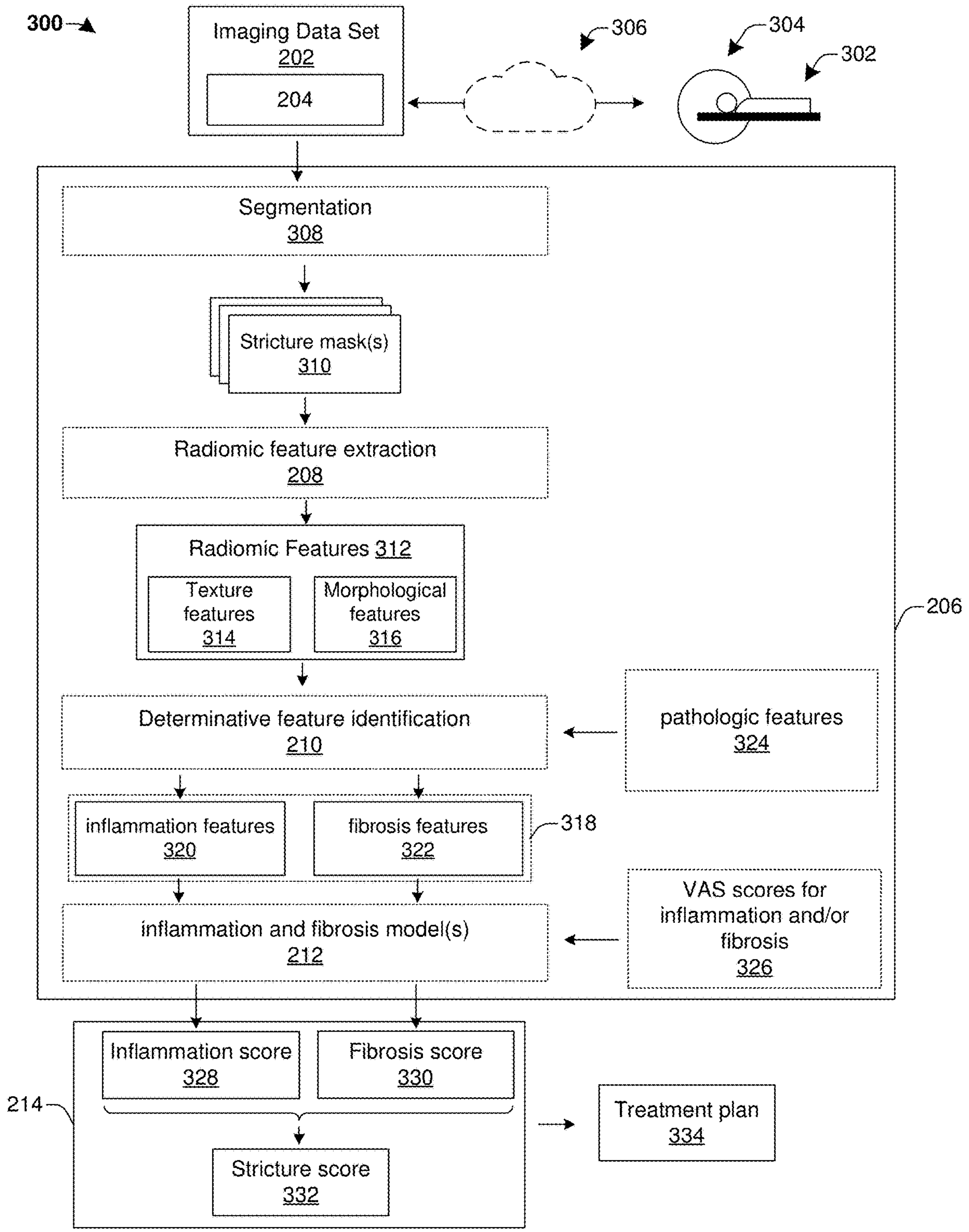
FIG. 3 illustrates a block diagram of some embodiments corresponding to a method and/or apparatus for assessing an extent of inflammation and/or fibrosis within intestinal strictures.

FIG. 3 illustrates a block diagram 300 of some embodiments corresponding to a method and/or apparatus for assessing an extent of inflammation and/or fibrosis within intestinal strictures.

As shown in block diagram 300, a radiological imaging tool 304 is operated upon a patient 302 having Crohn's disease to generate one or more radiological images 204. In some embodiments, the one or more radiological images 204 may comprise two-dimensional (2D) images including a plurality of pixels respectively having an intensity. In some embodiments, the one or more radiological images 204 may comprise three-dimensional (3D) images including a plurality of voxels respectively having an intensity. In some embodiments, the one or more radiological images 204 may comprise a volume of images comprising a stack of 2D images that collective form a 3D image. The one or more radiological images 204 may be comprised within an imaging data set 202. In additional embodiments, a part of the one or more radiological images 204 within the imaging data set 202 may be obtained from an on-line data base 306.

In some embodiments, the radiological imaging tool 304 may comprise a magnetic resonance enterography (MRE) scanner. The MRE scanner uses a magnetic field to form radiological images of a patient's intestine (e.g., small intestine). In some embodiments, contrast materials may be administered to the patient 302 (e.g., orally and/or intravenously) prior to imaging by the MRE scanner. In other embodiments, the radiological imaging tool 304 may comprise a computed tomography enterography (CTE) scanner. The CTE scanner uses x-rays to form radiological images of a patient's intestine (e.g., small intestine). In some embodiments, contrast materials may be administered to the patient 302 (e.g., orally and/or intravenously) prior to imaging by the CTE scanner.

The imaging data set 202 is provided to a machine learning pipeline 206 comprising a plurality of machine learning stages (e.g., machine learning models). In some embodiments, the machine learning pipeline comprises a segmentation stage 308, a radiomic feature extraction stage 208, a determinative feature identification stage 210, and an inflammation and fibrosis model stage 212.

The segmentation stage 308 is configured to identify one or more regions of interest (ROI) within the one or more radiological images 204. The one or more ROI respectively comprise an intestinal stricture. In some embodiments, the segmentation stage 308 may be configured to generate one or more stricture masks 310 from the one or more radiological images 204. The one or more stricture masks 310 comprise data from specific regions of the one or more radiological images 204 while excluding data from other regions. In some embodiments, a plurality of stricture masks 310 may respectively focus on an intestinal stricture within a radiological image. For example, a radiological image having two intestinal strictures may be used to form a first stricture mask comprising the first intestinal stricture (and not the second intestinal stricture) and a second stricture mask comprising the second intestinal stricture (and not the first intestinal stricture).

The radiomic feature extraction stage 208 is configured to extract a plurality of radiomic features 312 from the one or more stricture masks 310. In some embodiments, the plurality of radiomic features 312 may comprise texture features 314 and/or morphological features 316 that describe a shape, size, and/or the like of an intestinal stricture. In various embodiments, the plurality of radiomic features 312 may comprise gray level co-occurrence matrix (GLCM) features (e.g., Haralick features), Law's features, Gabor features, fractals, Law's masks, Gabor filters, Sobel operations, wavelet transforms, wavelet packets, or the like. In some additional embodiments, the plurality of radiomic features 312 may further comprise a statistical technique applied to a radiomic metric (e.g., a GLCM, a Gabor metric, etc.) over a plurality of pixels. For example, an entropy may be determined for a plurality of pixels within a stricture mask, and a mean of the entropy may be determined for the plurality of pixels to determine a first radiomic heterogeneity feature. In various embodiments, the statistical techniques may comprise a mean, a medium, a standard deviation, a skew, a Kurtosis, etc.

The determinative feature identification stage 210 is configured to identify a plurality of determinative features 318 from the plurality of radiomic features 312. The plurality of determinative features 318 comprise radiomic features that are important in determining an extent of fibrosis and/or inflammation within an intestinal stricture. In some embodiments, the plurality of determinative features 318 may comprise a plurality of inflammation features 320 and/or a plurality of fibrosis features 322. The plurality of inflammation features 320 comprise a subset of the plurality of radiomic features 312 that are most determinative in identifying inflammation within an intestinal stricture. The plurality of fibrosis features 322 comprise a subset of the plurality of radiomic features 312 that are most determinative in identifying fibrosis within an intestinal stricture. In various embodiments, the plurality of inflammation features 320 and/or the plurality of fibrosis features 322 may be identified using a QDA model, a t-test, a random forest algorithm, a minimum redundancy maximum relevance (mRMR) algorithm, or the like.

In some embodiments, the plurality of determinative features 318 may be selected to correspond to one or more pathological features 324 used to analyze inflammation and/or fibrosis within a pathological sample of a corresponding intestinal stricture. For example, a pathological sample may be taken from an intestinal stricture and subjected to Stenosis Therapy and Research (STAR) scoring/grading. The STAR scoring uses a number of pathological features 324 to determine inflammation and/or fibrosis within the pathological sample. In some embodiments, the pathological features 324 used in the STAR scoring may be provided to the determinative feature identification stage 210 to enable selection of the plurality of determinative features 318 for the intestinal stricture corresponding to the pathological sample. In such embodiments, the determinative feature identification stage 210 may select radiomic features that are associated with the different ones of the pathological features 324. For example, the determinative feature identification stage 210 may select radiomic features that correspond to one or more fibrotic pathological factors such as mucosal fibrosis, subserosal adventitia fibrosis, or the like. By selecting radiomic features that correspond to different ones of the pathological features 324, the determinative feature identification stage 210 may be able to select the plurality of determinative features 318 to accurately determine an extent of fibrosis and/or inflammation within an intestinal stricture since the radiomic features correspond to pathological features 324 that are known to identify fibrosis and/or inflammation within the interstitial stricture.

The inflammation and fibrosis model stage 212 is configured to operate upon the plurality of determinative features 318 to determine an extent of inflammation and/or fibrosis within an intestinal stricture. In some embodiments, the inflammation and fibrosis model stage 212 is configured to operate upon the plurality of inflammation features 320 to generate an inflammation score 218 and/or to operate upon the plurality of fibrosis features 322 to generate a fibrosis score 330. The inflammation score 328 is a numeric indicator (e.g., having a numeric value between 0 and 1) relating to an extent of (e.g., a percentage of) inflammation within an intestinal stricture. For example, a high inflammation score may indicate that an intestinal stricture is largely due to inflammation, while a low inflammation score may indicate that the intestinal stricture is largely due to fibrosis. Similarly, the fibrosis score 330 is a numeric indicator (e.g., having a numeric value between 0 and 1) relating an extent of (e.g., a percentage of) fibrosis within an intestinal stricture. For example, a high fibrosis score may indicate that an intestinal stricture is largely due to fibrosis, while a low fibrosis score may indicate that the intestinal stricture is largely due to inflammation. In some embodiments, the inflammation score 328 and the fibrosis score 330 may be collectively used to generate a stricture score 332 that denotes an extent of (e.g., a percentage of) fibrosis and/or inflammation within an intestinal stricture.

In some embodiments, an output of the inflammation and fibrosis model stage 212 may be augmented by combining a result of the inflammation and fibrosis model stage 212 with a visual analog score (VAS) 326 for inflammation and/or fibrosis. In some embodiments, the augmentation may be performed by the inflammation and fibrosis model stage 212, while in other embodiments the augmentation may be performed by a downstream stage (not shown). The VAS score 326 may be determined from the radiological image (e.g., an MRE image) by an expert radiologist.

In some embodiments, a treatment plan 334 may be generated based upon the inflammation score 328 and/or the fibrosis score 330. For example, if the inflammation score 328 and/or the fibrosis score 330 indicate that an intestinal stricture is largely inflammation the treatment plan 334 may include non-invasive treatment such as the use of anti-inflammatory medication to reduce a size of the intestinal stricture. Alternatively, if the inflammation score 328 and/or the fibrosis score 330 indicate that an intestinal stricture is largely fibrosis the treatment plan 334 may include surgical resection of the intestinal stricture.

Figure 4:
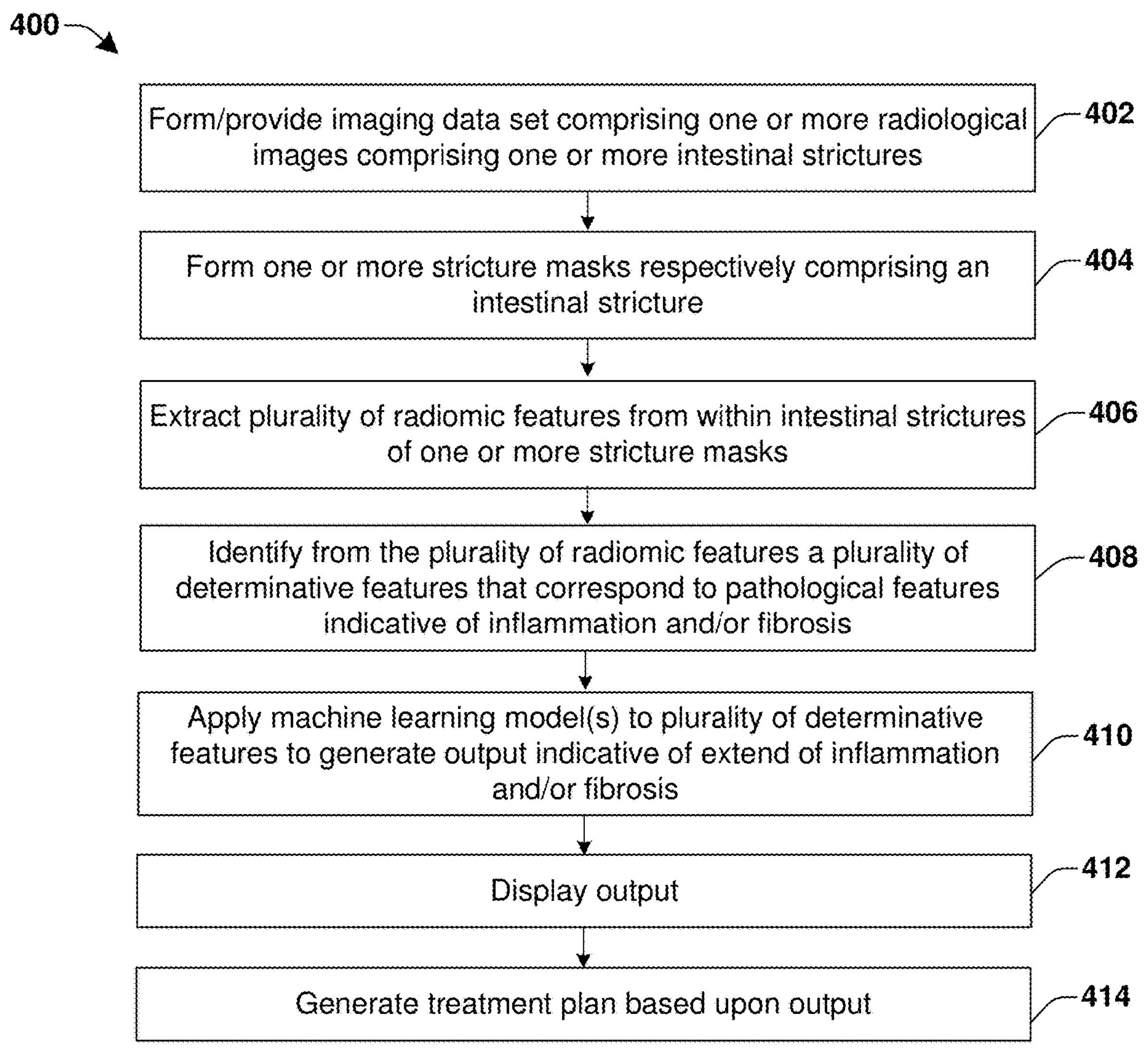
FIG. 4 illustrates some additional embodiments of a method for assessing an extent of inflammation and/or fibrosis within intestinal strictures.

FIG. 4 illustrates some additional embodiments of a method 400 for assessing an extent of inflammation and/or fibrosis within intestinal strictures.

At act 402, an imaging data set is provided and/or formed to comprise one or more radiological images including one or more intestinal strictures.

At act 404, one or more stricture masks are formed from the one or more radiological images. The one or more strictures masks respectively comprise an intestinal stricture.

At act 406, a plurality of radiomic features are extracted from the intestinal strictures of the one or more stricture masks. The plurality of radiomic features comprise texture features describing a texture associated with an intestinal stricture and/or morphological features describing a morphology associated with an intestinal stricture.

At act 408, a plurality of determinative features are extracted from the plurality of radiomic features. The plurality of determinative features are a subset of the plurality of radiomic features that are most determinative in identifying fibrosis and/or inflammation within an intestinal stricture. In some embodiments, a first plurality of determinative inflammation features may be extracted from an MRE image, a first plurality of determinative fibrosis features may be extracted from an MRE image, a second plurality of determinative inflammation features may be extracted from a CTE image, and a second plurality of determinative fibrosis features may be extracted from a CTE image. In some embodiments, the plurality of determinative features may be selected to correlate with pathological features that have been identified to be indicative of inflammation and/or fibrosis within the intestinal stricture.

At act 410, a machine learning model is applied to the plurality of determinative features to generate an output that identifies inflammation and/or fibrosis within the intestinal stricture. In some embodiments, the first plurality of determinative inflammation features or the second plurality of determinative inflammation features may be used to generate an inflammation score that is indicative of inflammation within an intestinal stricture. In some embodiments, the first plurality of determinative fibrosis features or the second plurality of determinative fibrosis features may be used to generate a fibrosis score that is indicative of fibrosis within an intestinal stricture.

At act 412, the output is displayed. In various embodiments, the output may comprise the fibrosis score, the inflammation score, a stricture score determined from the fibrosis score and/or the inflammation score, a percentage of inflammation and/or fibrosis within an intestinal stricture determined from the fibrosis score and/or the inflammation score, or the like.

At act 414, a treatment plan is generated based upon the output. In various embodiments, the treatment plan may be subsequently applied to a patient to treat the intestinal stricture.

It has been appreciated that the signatures of MRE image and CTE images are different. Because of the different signatures, a set of determinative features used to compute an inflammation score and a fibrosis score from an MRE image may be different than a set of determinative features used to compute an inflammation score and a fibrosis score from a CTE image.

Figure 5A:
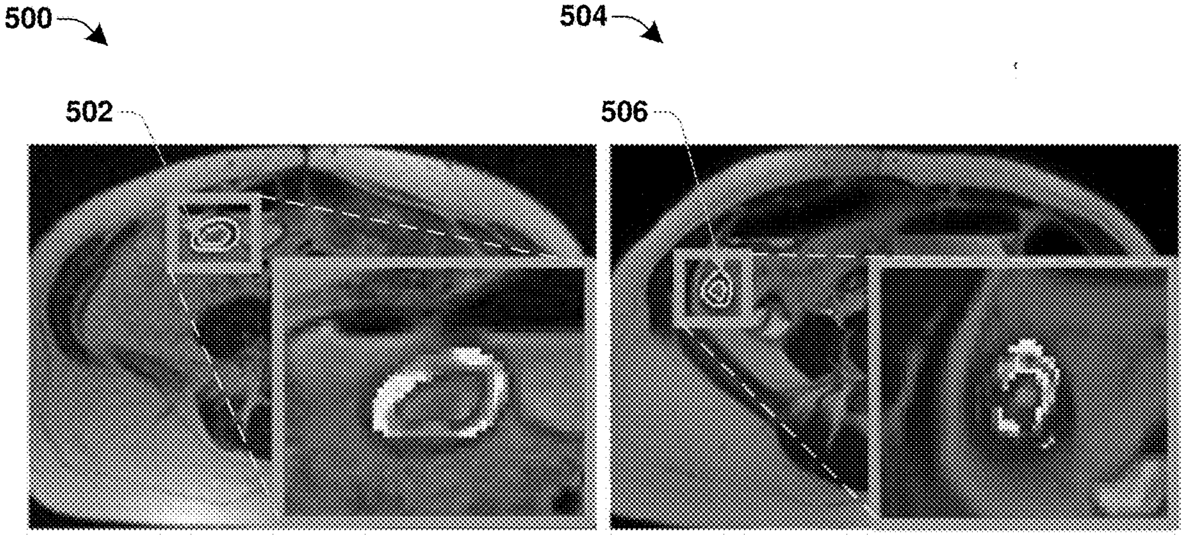
FIG. 5A illustrates some exemplary magnetic resonance enterography (MRE) images showing intestinal strictures having varying degrees of inflammation.

FIG. 5A illustrates some exemplary MRE images showing intestinal strictures having varying degrees of inflammation. In some embodiments, the MRE images may be part of an image volume comprising a plurality of 2D MRE images that make up a 3D MRE image.

The MRE images 500 and 504 respectively comprise a plurality of pixel regions (e.g., pixels) with each pixel region having an intensity. MRE images 500 and 504 also comprise intestinal strictures, 502 and 506, respectively. The intestinal strictures, 502 and 506, comprise a plurality of intestinal pixel regions. The plurality of intestinal pixel regions have different values of a radiomic feature, which are illustrated as different colors. In general, warm colors (e.g., red, yellow, orange) denote high radiomic values, while cool colors (e.g., blue, purple, green) denote low radiomic values. For example, in some embodiments the different colors of intestinal pixel regions may correspond to different values of a gray level co-occurrence matrix (GLCM) pattern. In such embodiments, the GLCM pattern may measure heterogeneity by determining a distribution of co-occurring pixel values (e.g., Hounsfield units) at a given offset, so as to determine how closely associated image signals within a local region are and thus give a measure of heterogeneity within a stricture mask As shown in MRE image 500, intestinal stricture 502 comprises radiomic features generally having relatively high values. The relatively high values correspond to a low severity of inflammation. In contrast, intestinal stricture 506 includes radiomic features generally having relatively low values. The relatively low values correspond to a high severity of inflammation. It will be appreciated that in alternative embodiments, relatively low radiomic values may correspond to a low severity of inflammation and relatively high radiomic values may correspond to a high severity of inflammation.

Figure 5B:
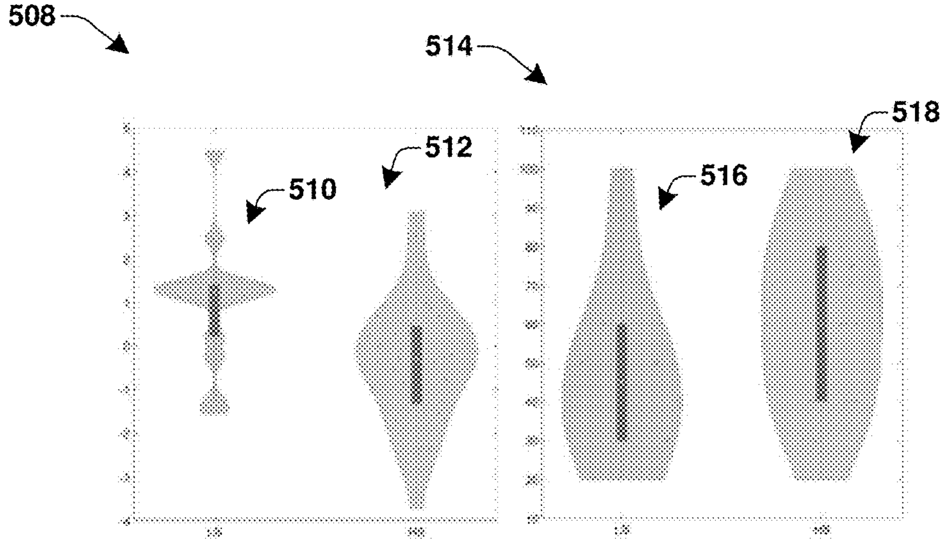
FIG. 5B illustrates violin plots showing an example of radiomic feature values and corresponding VAS (visual analog score) feature values associated with inflammation in the MRE images of FIG. 5A.

FIG. 5B illustrates violin plots showing an example of radiomic feature values and corresponding VAS (visual analog score) feature values associated with inflammation in the MRE images of FIG. 5A.

As shown in violin plot 508, a first value for a GLCM pattern 510 that is relatively high corresponds to a low severity of inflammation and a second value for a GLCM pattern 512 that is relatively low corresponds to a high severity of inflammation. Furthermore, as shown in violin plot 514, the first value for the GLCM pattern 510 and the second value for the GLCM pattern 512 correspond to VAS (visual analog score) values 516 and 518 taken from a visual assessment of the intestinal strictures so as to get good agreement between the radiomic features and the VAS features.

In some embodiments, a first plurality of determinative inflammation features that may be extracted from an MRE image comprise patterned based features, such as a gray level co-occurrence matrix (GLCM) pattern. In other embodiments, the first plurality of determinative inflammation features may comprise a median of a Law's feature (e.g., having convolution kernels comprising L3 E3 S3), a Kurtosis of a Gabor feature (e.g., having an XY orientation of 1.963, an XZ orientation of 2.356, a lambda of 2.705, and a BW=1), a median of a gradient difference variance (e.g., having a window size 5 and orientation 1), a skewness of a Law's feature (e.g., having convolution kernels comprising L5 R5 W5), a skewness of a Law's feature (e.g., having convolution kernels comprising W5 W5 R5), a skewness of a Law's feature (e.g., having convolution kernels comprising R5 W5 L5), a skewness of a gradient second information measure of correlation (e.g., having a window size 5 and orientation 0), and/or a skewness of a Law's feature (e.g., having convolution kernels comprising L5 W5 E5). In yet other embodiments, the first plurality of determinative inflammation features may comprise a skewness of a Gabor feature (e.g., having an XY orientation of 1.963, an XZ orientation of 2.356, a lambda of 2.705, and a BW=1), a kurtosis of a Law's feature (e.g., having convolution kernels S5 R5 L5), a median of a Law's feature (e.g., having convolution kernels S3 L3 E3), and/or a median of a Haralick energy feature (e.g., having a window size of 7).

Figure 6A:
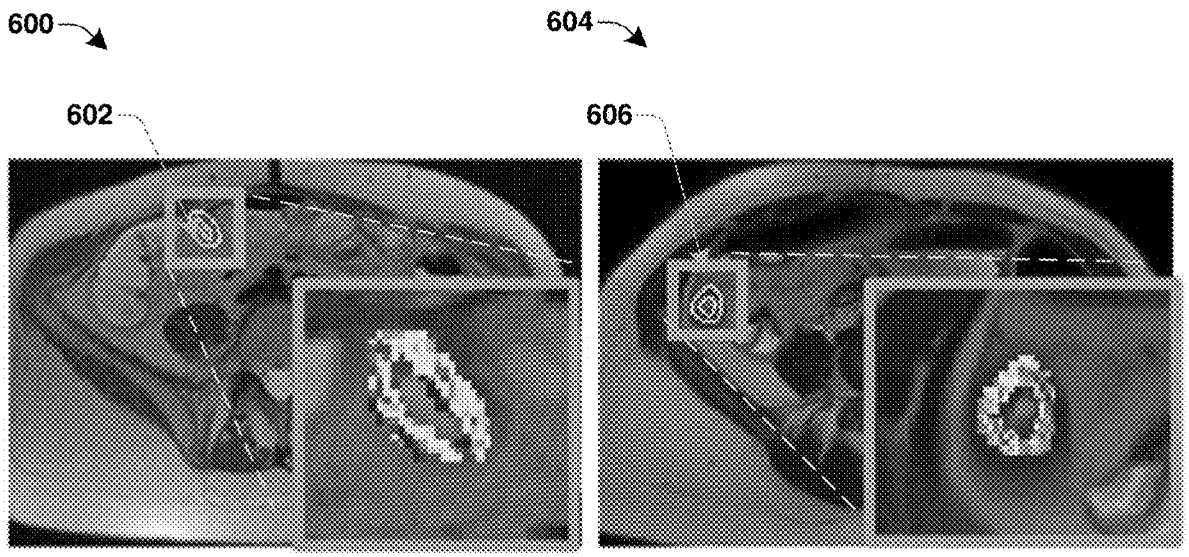
FIG. 6A illustrates some exemplary MRE images showing intestinal strictures having varying degrees of fibrosis.

FIG. 6A illustrates some exemplary MRE images showing intestinal strictures having varying degrees of fibrosis. In some embodiments, the MRE images may be part of an image volume comprising a plurality of 2D MRE images that make up a 3D MRE image.

The MRE images 600 and 604 respectively comprise a plurality of pixel regions. MRE images 600 and 604 also comprise intestinal strictures, 602 and 606, respectively. The intestinal strictures, 602 and 606, comprise a plurality of intestinal pixel regions. In some embodiments the different colors of intestinal pixel regions may correspond to different values of a Gabor wavelet. Intestinal stricture 602 comprises radiomic features generally having relatively low values that correspond to a low severity of fibrosis. In contrast, intestinal stricture 606 includes radiomic features generally having relatively high values that correspond to a high severity of fibrosis.

Figure 6B:
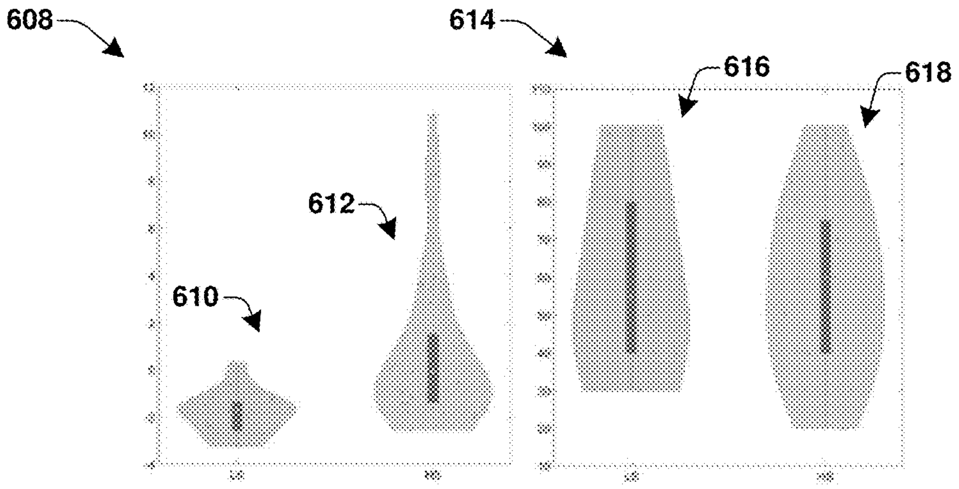
FIG. 6B illustrates violin plots showing an example of radiomic feature values and corresponding VAS feature values associated with fibrosis in the MRE images of FIG. 6A.

FIG. 6B illustrates violin plots showing an example of radiomic feature values and corresponding VAS feature values associated with fibrosis in the MRE images of FIG. 6A.

As shown in violin plot 608, a first value for a Gabor wavelet 610 that is relatively low corresponds to a low severity of inflammation and a second value for a Gabor wavelet 612 that is relatively low corresponds to a high severity of inflammation. Furthermore, as shown in violin plot 614, the first value for the Gabor wavelet 610 and the second value for the Gabor wavelet 612 correspond to VAS values 616 and 618 taken from a visual assessment of the intestinal stricture.

In some embodiments, a first plurality of determinative fibrosis features that may be extracted from an MRE image comprise wavelet-based features, such as a Gabor wavelet. In other embodiments, the first plurality of determinative fibrosis features may comprise a skewness of a Gabor feature (e.g., having an XY orientation of 1.571, an XZ orientation of 0.785, a lambda of 2.075, and a BW=1), a skewness of a Law's feature (e.g., having convolution kernels comprising S3 S3), a kurtosis of a Law's feature (e.g., having convolution kernels comprising E5 R5 L5), a kurtosis of a Gray mean feature (e.g., having a window size of 9), a median gradient sum of squares variance (e.g., having a window size of 9 and orientation 0), a variance of a Gray range (e.g., having a window size of 9), a skewness of gradient entropy (e.g., having a window size of 3 and orientation 0), and/or a median of gradient angular second moment (e.g., having a window size of 5 and orientation 0). In yet other embodiments, the first plurality of determinative fibrosis features may comprise a skewness of a Law's feature (e.g., having convolution kernels comprising S5 W5 R5), a skewness of a Law's feature (e.g., having convolution kernels comprising R5 W5 W5), a median of a Law's feature (e.g., having convolution kernels comprising R5 W5), and/or a skewness of a Haralick inertia feature (e.g., having a window size of 11).

Figure 7A:
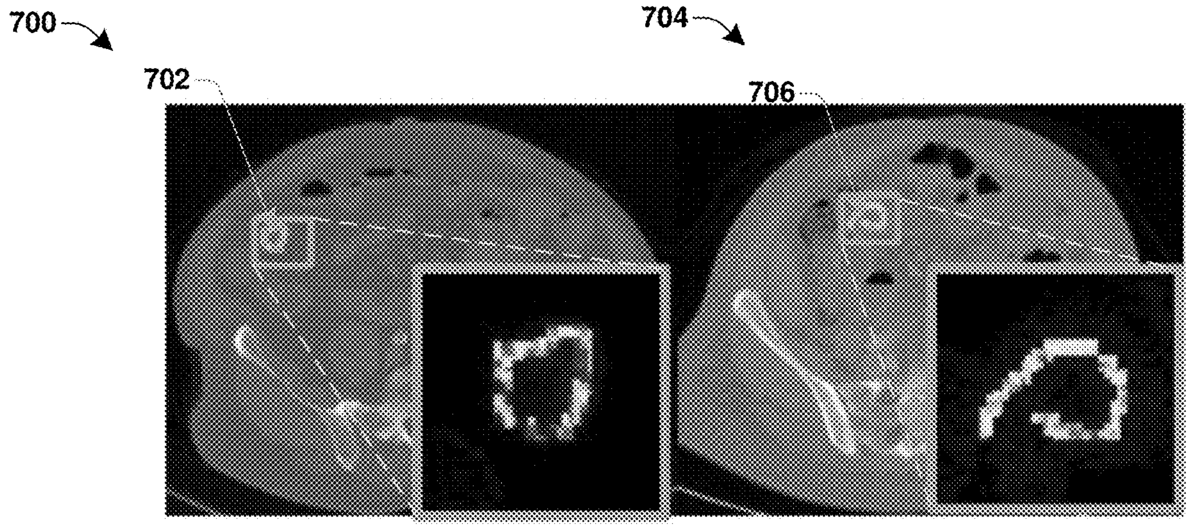
FIG. 7A illustrates some exemplary computed tomography enterography (CTE) images showing intestinal strictures with varying degrees of inflammation.

FIG. 7A illustrates some exemplary CTE images showing intestinal strictures having varying degrees of inflammation. In some embodiments, the CTE images may be part of an image volume comprising a plurality of 2D CTE images that make up a 3D CTE image.

The CTE images 700 and 704 respectively comprise a plurality of pixel regions. CTE images 700 and 704 also comprise intestinal strictures, 702 and 706, respectively. The intestinal strictures, 702 and 706, comprise a plurality of intestinal pixel regions. In some embodiments the different colors of intestinal pixel regions may correspond to different values of a Sobel pattern. Intestinal stricture 702 comprises radiomic features generally having relatively low values that correspond to a low severity of inflammation. In contrast, intestinal stricture 706 includes radiomic features generally having relatively high values that correspond to a high severity of inflammation.

Figure 7B:
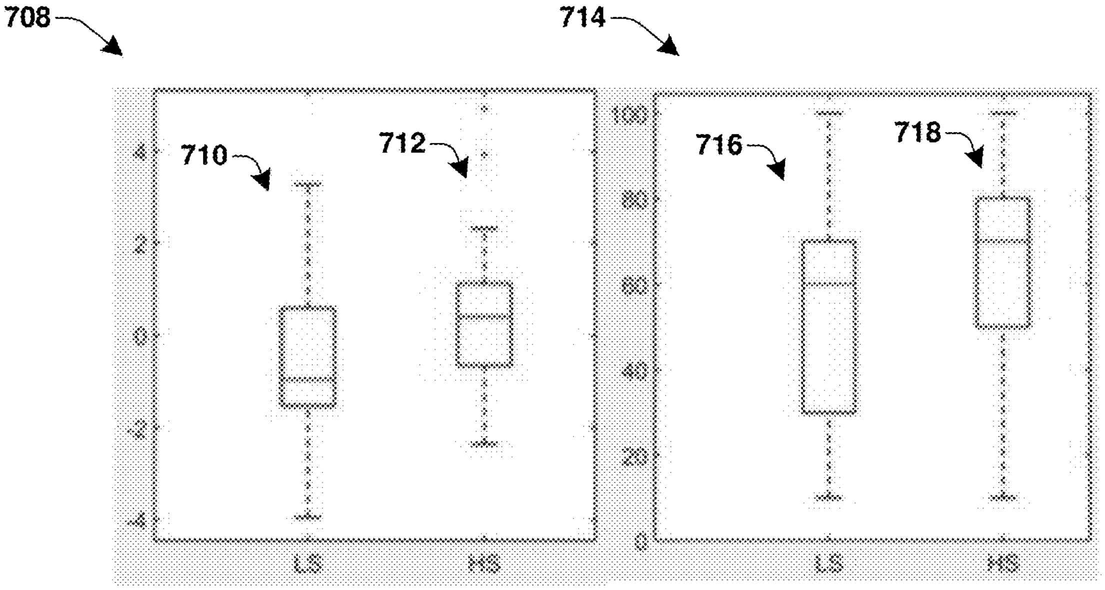
FIG. 7B illustrates box plots showing an example of radiomic feature values and corresponding VAS feature values associated with inflammation in the CTE images of FIG. 7A.

FIG. 7B illustrates box plots, 710 and 716, showing an example of radiomic feature values and corresponding VAS feature values associated with inflammation in the CTE images of FIG. 7A.

As shown in box plot 708, a first value for a Sobel pattern 710 that is relatively low corresponds to a low severity of inflammation and a second value for a Sobel pattern 712 that is relatively high corresponds to a high severity of inflammation. Furthermore, as shown in box plot 714, the first value for the Sobel pattern 710 and the second value for the Sobel pattern 712 correspond to VAS values 716 and 718 taken from a visual assessment of the intestinal strictures.

In some embodiments, the second plurality of determinative inflammation features that may be extracted from a CTE image comprise patterned based features, such as a Sobel pattern. In other embodiments, the second plurality of determinative inflammation features may comprise a median of a Gradient Sobel feature (e.g., along an xz plane), a skewness of a Law's feature (e.g., having convolution kernels R5 R5 S5), a variance of a Gradient Sobel feature (e.g., along the zy plane), a kurtosis of a Gabor feature (e.g., having an XY orientation of 1.963, an XZ orientation of 0.000, a lambda of 2.075, and a BW=1), a skewness of a Haralick energy feature (e.g., having a window size of 9), a skewness of a Law's feature (e.g., having convolution kernels comprising L5 R5 R5), a skewness of a Law's feature (e.g., having convolution kernels comprising R5 E5 L5), a median of a Gabor feature (e.g., having an XY orientation of 1.178, an XZ orientation of 0.000, a lambda of 1.482, and a BW=1), a median of a Law's feature (e.g., having convolution kernels comprising W5 L5 S5), and/or a median of a Law's feature (e.g., having convolution kernels comprising L3 E3 L3). In yet other embodiments, the second plurality of determinative inflammation features may comprise a skewness of a Law's feature (e.g., having convolution kernels comprising L5 S5 R5), a kurtosis of a Haralick feature (e.g., having info2 and a window size of 3), a skewness of a Law's feature (e.g., having convolution kernels S5 E5 L5), and/or a median of a Gray median (e.g., having a window size of 3).

Figure 8A:
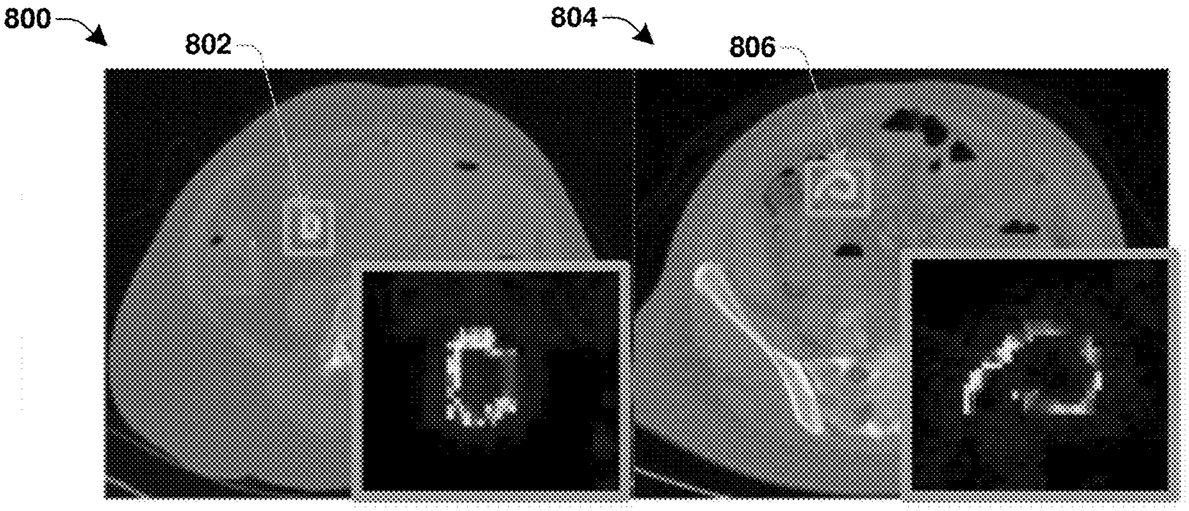
FIG. 8A illustrates some exemplary CTE images showing intestinal strictures having varying degrees of fibrosis.

FIG. 8A illustrates CTE images showing intestinal strictures with varying degrees of fibrosis. In some embodiments, the CTE images may be part of an image volume comprising a plurality of 2D CTE images that make up a 3D CTE image.

The CTE images 800 and 804 respectively comprise a plurality of pixel regions. CTE images 800 and 804 also comprise intestinal strictures, 802 and 806, respectively. The intestinal strictures, 802 and 806, comprise a plurality of intestinal pixel regions. The plurality of intestinal pixel regions have different values of a radiomic feature, which are illustrated as different colors. In some embodiments the different colors of intestinal pixel regions may correspond to different values of a Gabor wavelet. Intestinal stricture 802 comprises radiomic features generally having relatively high values that correspond to a low severity of inflammation. In contrast, intestinal stricture 806 includes radiomic features generally having relatively low values that correspond to a high severity of inflammation. It will be appreciated that in alternative embodiments, relatively low radiomic values may correspond to a low severity of inflammation and relatively high radiomic values may correspond to a high severity of inflammation.

Figure 8B:
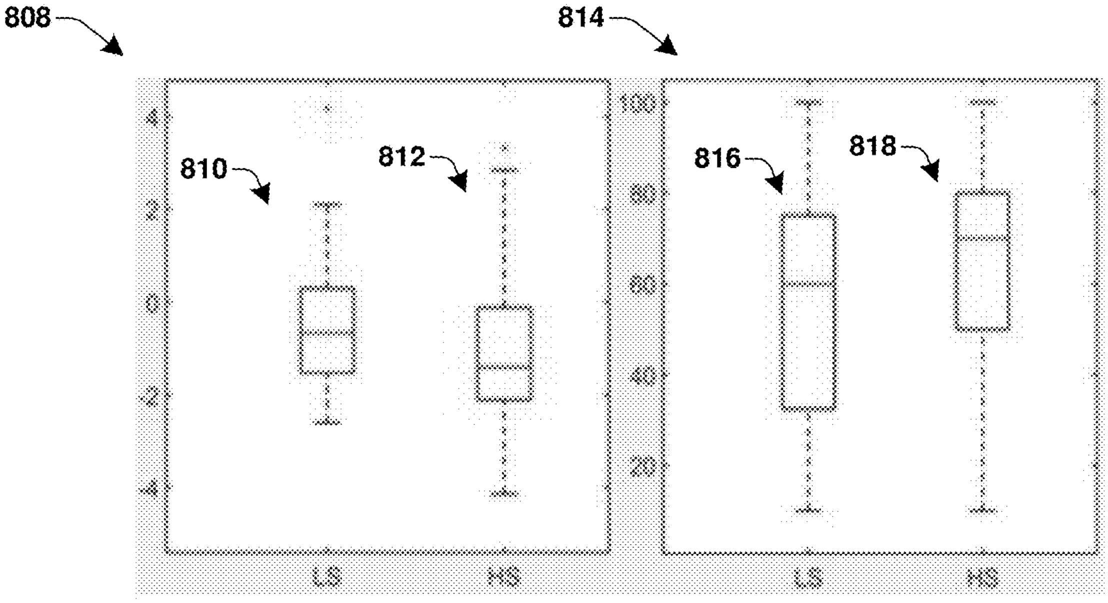
FIG. 8B illustrates box plots showing an example of radiomic feature values and corresponding VAS feature values associated with fibrosis in the CTE images of FIG. 8A.

FIG. 8B illustrates box plots, 810 and 816, showing an example of radiomic feature values and a corresponding VAS feature values associated with fibrosis in the CTE images of FIG. 8A.

As shown in box plot 808, a first value for a Gabor wavelet 810 that is relatively high corresponds to a low severity of fibrosis and a second value for a Gabor wavelet 812 that is relatively low corresponds to a high severity of fibrosis. Furthermore, as shown in box plot 814, the first value for the Gabor wavelet 810 and the second value for the Gabor wavelet 812 correspond to VAS values 816 and 818 taken from a visual assessment of the intestinal strictures.

In some embodiments, a second plurality of determinative fibrosis features may comprise patterned wavelet-based features, such as a Gabor wavelet. In other embodiments, the second plurality of determinative fibrosis features may comprise a skewness of a Law's feature (e.g., having convolution kernels comprising L5 W5 S5), a median of a Gabor feature (e.g., having an XY orientation of 0.000, an XZ orientation of 1.571, a lambda of 2.668, and a BW=1), a median of a Gray range feature (e.g., having a window size of 7), a median of a Haralick sum variance (e.g., having a window size of 9), a median of a Law's feature (e.g., having convolution kernels L3 L3 S3), a kurtosis of a Haralick energy feature (e.g., having a window size of 3), a median of a Law's feature (e.g., having convolution kernels comprising W5 E5 R5), a median of a Gabor feature (e.g., having an XY orientation of 0.000, an XZ orientation of 0.000, a lambda of 3.261, and a BW=1), a variance of a Law's feature (e.g., having convolution kernels comprising L5 R5 L5), and/or a median of a Law's feature (e.g., having convolution kernels comprising L5 R5 L5). In yet other embodiments, the second plurality of determinative fibrosis features may comprise a median of a Gabor feature (e.g., having an XY orientation of 0.000, an XZ orientation of 1.571, and a lambda of 2.668), a Kurtosis of a Law's feature (e.g., having convolution kernels comprising L5 S5 L5), a skewness of a Law's feature (e.g., having convolution kernels comprising L5 R5 L5), and/or a median of a Law's feature (e.g., having convolution kernels comprising W5 E5 E5).

Figure 9:
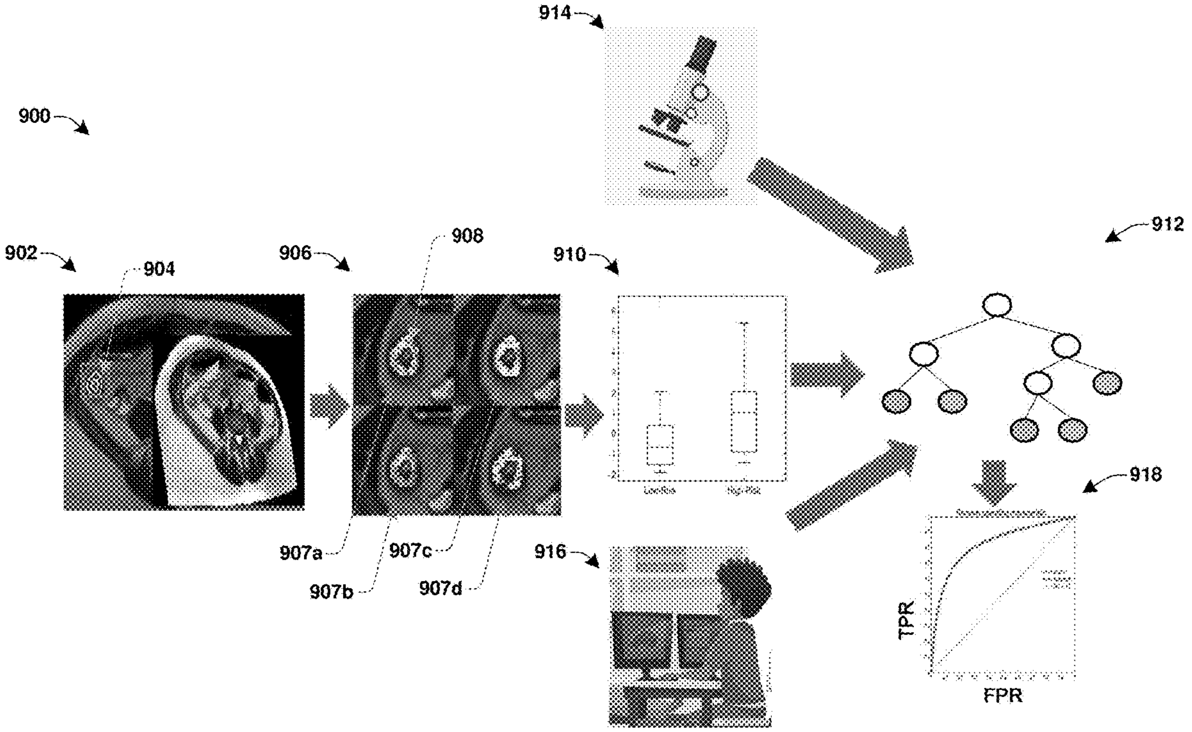
FIG. 9 illustrates a diagram showing some additional embodiments corresponding to a method and/or apparatus for assessing inflammation and/or fibrosis within intestinal strictures.

FIG. 9 illustrates a diagram 900 showing some additional embodiments corresponding to a method and/or apparatus for assessing an extent of inflammation and/or fibrosis within intestinal strictures.

As shown in diagram 900, a radiological image 902 is provided from a patient having Crohn's disease. The radiological image 902 may include and/or be an image of a body cavity having an intestinal stricture 904. The radiological image 902 comprises a plurality of pixels respectively having a value. In some embodiments, the radiological image 902 may be from a patient that had also undergone surgical resection of the intestinal stricture 904 and that had provided surgically resected tissue to a pathologist that performed pathological analysis of the surgically resected tissue (e.g., according to Histopathological Stensosi Therapy and Research (STAR) scoring).

One or more intestinal stricture masks 906 may be generated from the radiological image 902. A plurality of radiomic features 907*a*-907*d* are extracted from the intestinal stricture masks 906. In some embodiments, the plurality of radiomic features 907*a*-907*d* may comprise texture features that describe a measure of consistency of signal values (e.g., Hounsfield units) between different points 908 (e.g., pixels, voxels, etc.) within the one or more regions associated with an intestinal stricture. In some embodiments, the plurality of radiomic features 312 may comprise morphological features that describe a shape, size, or the like associated with an intestinal stricture. For each of the radiomic features 907*a*-907*d* a value 910 of the radiomic feature are determined.

The plurality of radiomic features 907*a*-907*d* are provided to a machine learning classifier 912. In some embodiments, a plurality of pathological features 914 are also provided to the machine learning classifier 912. The plurality of pathological features 914 are features that have been identified by an expert pathologist as being indicative of inflammation and/or fibrosis within a pathology sample of an intestinal stricture corresponding to a radiological image of the intestinal stricture. In some embodiments, the machine learning classifier 912 may be configured to correlate (i.e., associate) the plurality of radiomic features 907*a*-907*d* to the pathological features 914 to identify a set of determinative features from the plurality of radiomic features. In some embodiments, the pathological features 914 may comprise features used during STAR scoring of a specimen taken from a patient. In some embodiments, the features may be used to grade different aspects of a stricture such as active inflammation, chronic inflammation, fibrosis, muscle, or the like. By identifying the plurality of determinative features by correlating the plurality of radiomic features with pathological features, the plurality of determinative features are able to capture the STAR scoring components that were pathologically linked to inflammation and/or fibrosis within the intestinal stricture, thereby linking the output of the machine learning classifier 912 to pathological analysis of inflammation and/or fibrosis within the intestinal stricture.

In some embodiments, the output of the machine learning classifier 912 is validated. In some embodiments, the validation may be performed by comparing the output of the machine learning classifier 912 with a pathological ground truth. For example, the score generated by the validation may be performed by comparing the output of the machine learning classifier 912 with a STAR scoring determined by an expert pathologist. In some embodiments, the comparison of the output of the machine learning classifier 912 and the STAR score may be used to form a receiver operating characteristic (ROC) curve 918 illustrating an effectiveness of the machine learning classifier 912 in identifying an extent of inflammation and/or fibrosis in an intestinal stricture.

Figure 10A:
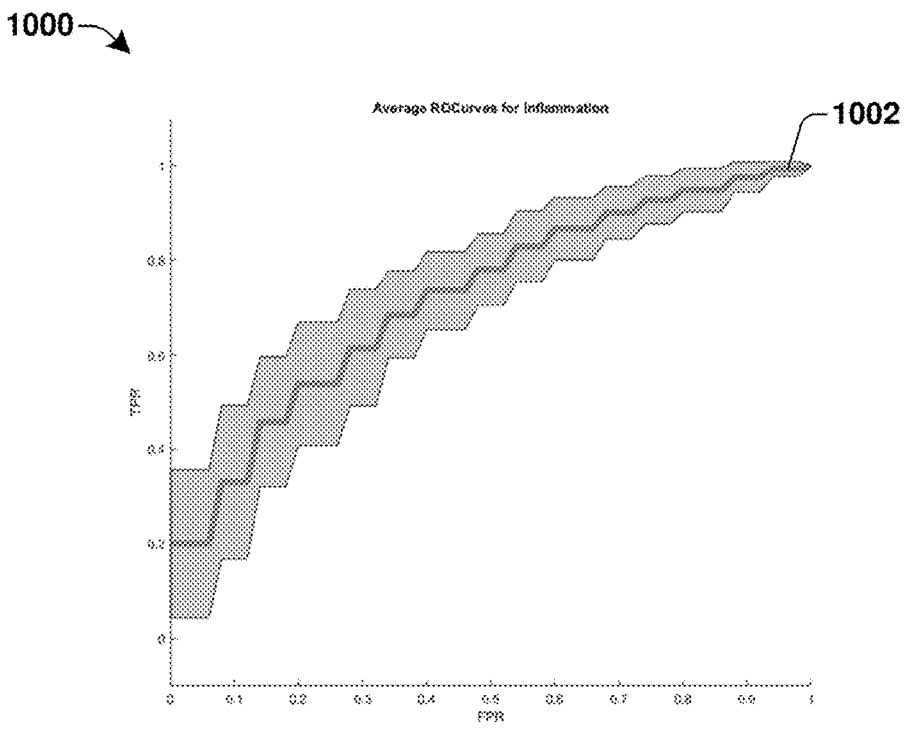
FIGS. 10A-10B illustrate graphs showing exemplary receiver operating characteristic (ROC) curves corresponding to the disclosed method and/or apparatus.
Figure 10B:
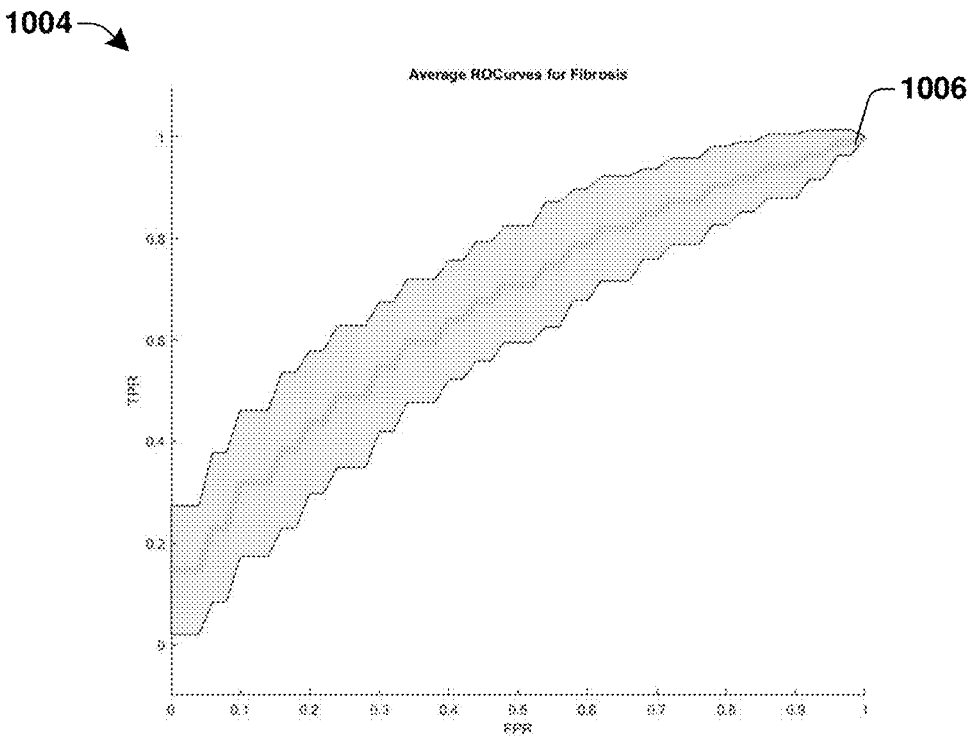

FIGS. 10A-10B illustrate graphs showing exemplary ROC curves corresponding to the disclosed method and/or apparatus.

FIG. 10A illustrates a graph 1000 of an exemplary ROC curve 1002 for inflammation. The ROC curve 1002 comprises a true positive rate (TPR) arranged along the y-axis and a false positive rate (FPR) arranged along the x-axis for different thresholds. As can be seen in ROC curve 1002, the area under curve (AUC) is approximately 0.73. The relative high AUC indicates that the disclosed machine learning pipeline generally performs well in predictive accuracy. In some additional embodiments, the disclosed machine learning pipeline may achieve an AUC on an ROC curve that is in a range of between approximately 0.67 and approximately 0.79.

FIG. 10B illustrates a graph 1004 of an exemplary ROC curve 1006 for fibrosis. The ROC curve 1006 comprises a TPR arranged along the y-axis and an FPR arranged along the x-axis for different thresholds. As can be seen in ROC curve 1006, the AUC is approximately 0.68. The relative high AUC indicates that the disclosed machine learning pipeline generally performs well in predictive accuracy. In some additional embodiments, the disclosed machine learning pipeline may achieve an AUC on an ROC that is in a range of between approximately 0.77 and approximately 0.83.

Figure 11:
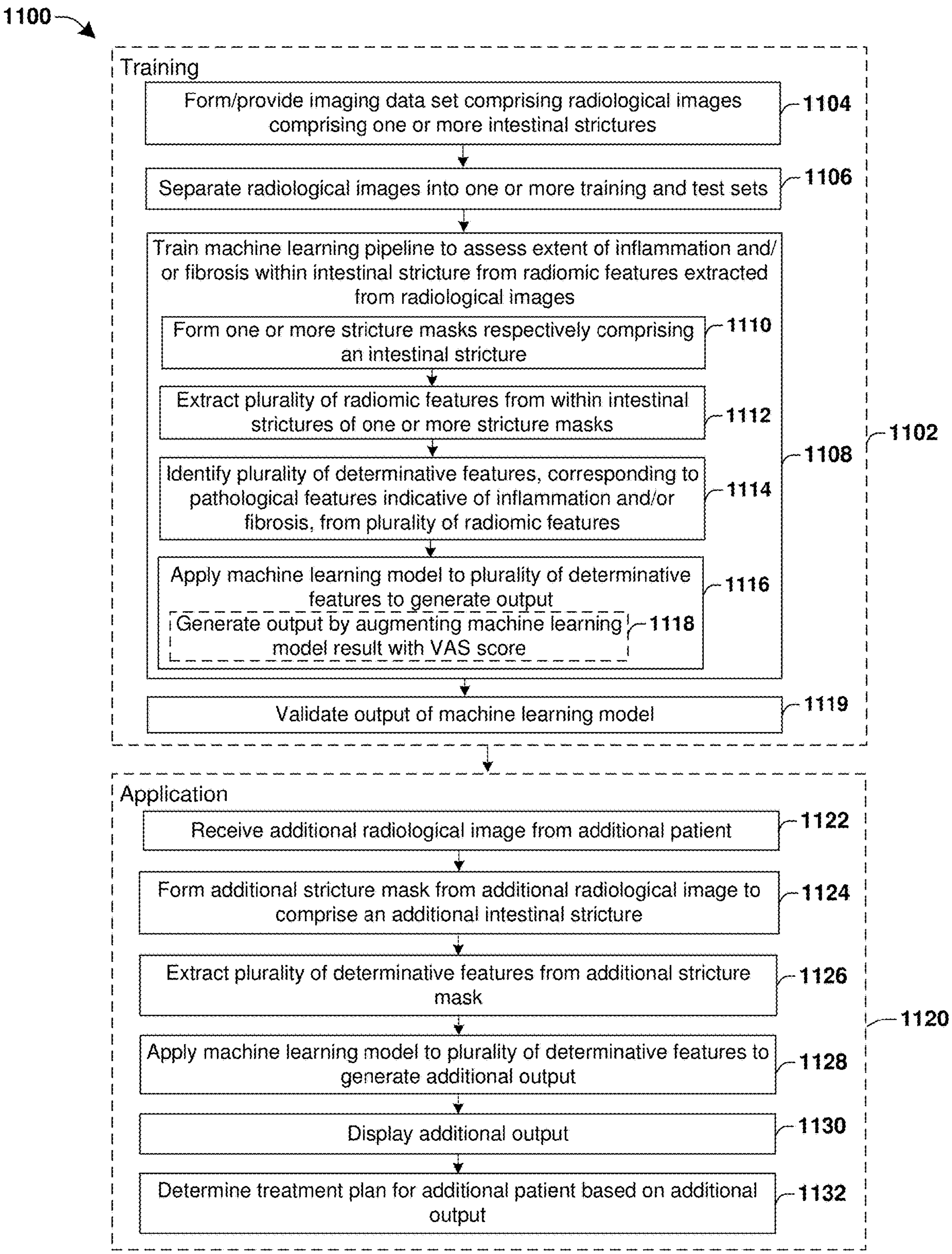
FIG. 11 illustrates some embodiments of a method of generating a machine learning pipeline that is configured to assess an extent of inflammation and/or fibrosis within intestinal strictures.

FIG. 11 illustrates some additional embodiments of a method 1100 of generating a machine learning pipeline that is configured to assess inflammation and/or fibrosis within intestinal strictures.

The method 1100 comprises a training phase 1102 and an application phase 1120. The training phase 1102 is configured to generate a machine learning pipeline that is able to assess an extent of inflammation and/or fibrosis using radiomic feature extracted from one or more radiological images. In some embodiments, the training phase 1102 may be performed according to acts 1104-1118.

At act 1104, an imaging data set is provided and/or formed to comprise a plurality of radiological images comprising one or more intestinal strictures. In some embodiments, the plurality of radiological images may be from patients that had also undergone surgical resection of the intestinal strictures and that had provided surgically resected tissue to a pathologist that performed pathological analysis of the surgically resected tissue (e.g., according to STAR scoring).

At act 1106, the plurality of radiological images within the imaging data set are separated into one or more training sets and one or more test sets. In some embodiments, the plurality of radiological images may be broken into k folds of data.

At act 1108, a machine learning pipeline is trained to generate an output, which is indicative of an extent of inflammation and/or fibrosis within an intestinal stricture, using radiomic features extracted from the plurality of radiological images. In some embodiments, the machine learning pipeline may operate on k−1 folds of data for training and the k fold of data for testing over a plurality of iterations (e.g., over 500 iterations). In some embodiments, each of the iterations may perform one or more operations of acts 1110-1118.

At act 1110, one or more strictures masks are formed from the plurality of radiological images. The one or more stricture masks respectively comprise an intestinal stricture.

At act 1112, a plurality of radiomic features are extracted from the one or more strictures. The plurality of radiomic features describe a texture and/or a morphology of one or more stricture masks.

At act 1114, a plurality of determinative features are extracted from the plurality of radiomic features. The plurality of determinative features are a subset of the plurality of radiomic features that are most determinative in identifying fibrosis and/or inflammation within an intestinal stricture. In some embodiments, the plurality of determinative features may be selected to correlate with pathological features that have been identified to be indicative of inflammation and/or fibrosis within the intestinal stricture. In some embodiments, the pathological features may comprise features used in STAR scoring of surgically resected tissue in an associated one of the plurality of radiological images.

At act 1116, a machine learning model is applied to the plurality of determinative features to generate an output that is indicative of an extent of inflammation and/or fibrosis within an intestinal stricture.

In some embodiments, at act 1118, the output may be generated by augmenting a result from the machine learning model with a visual analog score (VAS) of an associated one of the plurality of radiological images generated by a radiologist.

At act 1119, the output of the machine learning model may be validated. In some embodiments, the output of the machine learning model may be validated by comparing the output of the machine learning model to a pathological assessment of a tissue sample (e.g., a surgically resected tissue). For example, in some embodiments the output of the machine learning model may be validated by comparing the output of the machine learning model to a score generated by the STAR scoring of the surgically resected tissue (e.g., at act 1114).

The application phase 1120 is configured to utilize the machine learning pipeline that was trained in the training phase 1102 on one or more additional radiological images, which are taken from an additional patient having intestinal strictures. In some embodiments, the application phase 1120 may be performed according to acts 1122-1132.

At act 1122, an additional radiological image is obtained from an additional patient having Crohn's disease. The additional radiological image has one or more intestinal strictures. The additional patient is a patient that has not had surgical resection of the one or more intestinal strictures.

At act 1124, one or more additional strictures masks are formed from the additional radiological image. The one or more additional stricture masks respectively comprise an additional intestinal stricture.

At act 1126, a plurality of determinative features are extracted from the one or more additional strictures masks. In some embodiments, the plurality of determinative features are the determinative features identified at act 1114.

At act 1128, the machine learning model is applied to the plurality of determinative features to generate an additional output that is indicative of an extent of inflammation and/or fibrosis within the additional intestinal stricture.

At act 1130, the additional output is displayed.

At act 1132, a treatment plan is determined for the additional patient based upon the additional output. The treatment plan may be subsequently applied to the additional patient.

Figure 12:
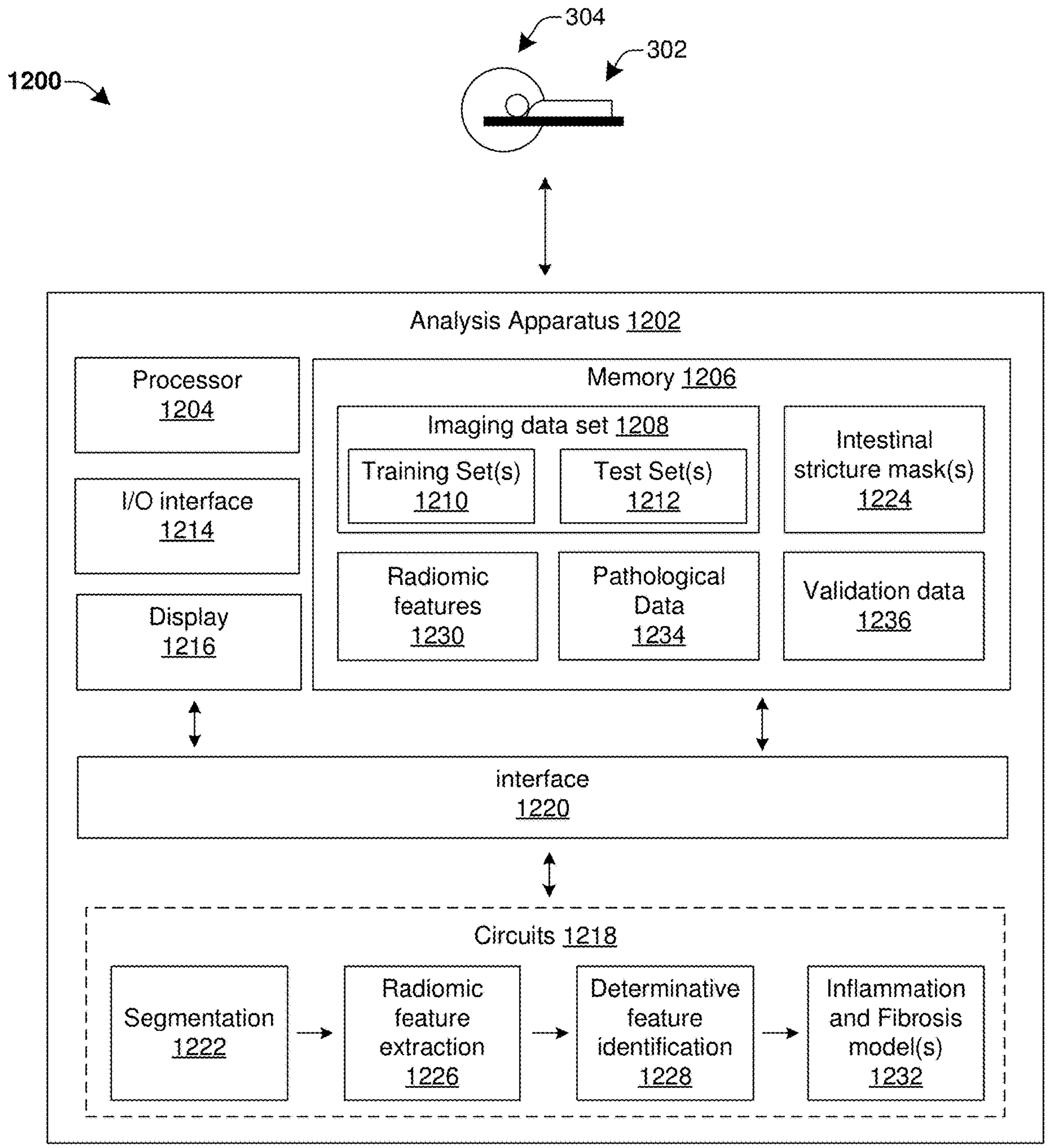
FIG. 12 illustrates some embodiments of a block diagram of an apparatus that is configured to assess an extent of inflammation and/or fibrosis within intestinal strictures.

FIG. 12 illustrates some embodiments of a block diagram of a system 1200 that is configured to assess an extent of inflammation and/or fibrosis within intestinal strictures.

The system 1200 comprises an analysis apparatus 1202 configured to assess an extent of inflammation and/or fibrosis within intestinal strictures based on a non-invasive method that utilizes radiological images. In some embodiments, the analysis apparatus may be coupled to a radiological imaging tool 304 configured to act upon a patient 302 having Crohn's disease. In various embodiments, the radiological imaging tool 304 may comprise an MRE scanner or a CTE scanner.

The analysis apparatus 1202 comprises a processor 1204 and a memory 1206. The processor 1204 can, in various embodiments, comprise circuitry such as, but not limited to, one or more single-core or multi-core processors. The processor 1204 can include any combination of general-purpose processors and dedicated processors (e.g., graphics processors, application processors, etc.). The processor(s) 1204 can be coupled with and/or can comprise memory (e.g., memory 1206) or storage and can be configured to execute instructions stored in the memory 1206 or storage to enable various apparatus, applications, or operating systems to perform operations and/or methods discussed herein.

Memory 1206 can be configured to store an imaging data set 1208 comprising one or more radiological images (e.g., CTE images, MRE images, etc.) for one or more patients having Crohn's disease. Each of the one or more radiological images can have a plurality of pixels, each pixel having an associated intensity. In some embodiments, memory 1206 can store one or more radiological images as one or more training set(s) 1210 for training a machine learning classifier and/or one or more test sets 1212 for validating the machine learning classifier.

The analysis apparatus 1202 also comprises an input/output (I/O) interface 1214 (e.g., associated with one or more I/O devices), a display 1216, a set of circuits 1218, and an interface 1220 that connects the processor 1204, the memory 1206, the I/O interface 1214, and the set of circuits 1218. The I/O interface 1214 can be configured to transfer data between the memory 1206, the processor 1204, the circuits 1218, and external devices, for example, a medical imaging device such as a CTE scanner, an MRE scanner, or the like.

The set of circuits 1218 can comprise a segmentation circuit 1222, a radiomic feature extraction circuit 1226, a determinative feature identification circuit 1228, and one or more fibrosis and/or inflammation models circuit 1232. In some embodiments, the set of circuits 1218 may comprise machine learning models comprising code run on a processor. In other embodiments, the set of circuits 1218 may comprise hardware components. The segmentation circuit 1222 is configured to access one or more radiological images and to identify intestinal strictures within the radiological images. Accessing the radiological image(s) can comprise accessing radiological image(s) within the imaging data set 1208 stored in memory 1206. In one embodiment, accessing the radiological image(s) can include accessing radiological image(s) stored in a data storage device, including a hard disk drive, a solid state device, a tape drive, or accessing radiological image(s) over a local area network, or accessing radiological image(s) over the internet. In some embodiments, the segmentation circuit 1222 is configured to generate intestinal stricture masks 1224 respectively comprising an intestinal stricture. In some embodiments, the intestinal stricture masks 1224 may be stored in the memory 1206.

In various embodiments, the radiomic feature extraction circuit 1226 is configured to extract a plurality of radiomic features 1230 from the intestinal stricture masks 1224. In some embodiment, the plurality of radiomic features 1230 may comprise texture features and/or morphological features. In some embodiments, the radiomic features may comprise features described above in relation to FIGS. 5A-8B. In some embodiments, the plurality of radiomic features 1230 may be stored in the memory 1206.

In various embodiments, the determinative feature identification circuit 1228 may be configured to identify a plurality of determinative radiomic features from the plurality of radiomic features 1230. In some embodiments, the determinative feature identification circuit 1228 may be configured to identify the plurality of determinative features by associating the plurality of radiomic features with pathological features 1234 identified by a pathologist to contribute to inflammation and/or fibrosis.

The one or more fibrosis and/or inflammation models circuit 1232 are configured to utilize the plurality of determinative features to generate an output that is indicative of an extent of inflammation and/or fibrosis within an intestinal stricture. In some embodiments, the one or more fibrosis and/or inflammation models circuit 1232 may be augmented with VAS data 1236 from a trained radiologist.

Example Use Case 1:

Purpose: Severe stricturing impacts a quarter of patients with Crohn's Disease (CD) during their lifetime, often requiring early targeted therapy and/or surgical resection to improve patient outcomes. Objective non-invasive evaluation for extent of inflammation and fibrosis within the stricture could significantly enhance treatment selection for stricturing CD. While MR enterography (MRE) is routinely used for high-resolution in vivo imaging of strictures, its utility has been limited to subjective, visual assessment alone. Results for a machine-reader evaluation of severe inflammation and fibrosis in CD strictures via quantitative radiomic features and expert radiologist scoring of MRE are presented.

Methods and Materials: IRB approved, retrospective, single center study included 51 patients (n=34 for discovery;

n=17 for hold-out validation) with strict definition of stricture on MRE for inclusion and confirmation on histopathology. All patients underwent surgery with 12 weeks of stricture diagnosis. Histopathological Stenosis Therapy & Research (STAR) scoring of specimens (range 0-100, scores>50=severe) was used as reference standard for both inflammation and fibrosis. In coordination with the scoring pathologist, an expert radiologist annotated the resected strictures on MRE and provided a global assessment of inflammation and Crohnic non-inflammatory findings (fibrosis) using a 0-100 visual analog score (VAS). In the discovery cohort, 1852 3D radiomic features were extracted from annotated strictures, from which the most relevant feature subsets were identified via cross-validated machine learning analysis in order to differentiate between (i) severe inflammation vs less severe, (ii) severe fibrosis vs less severe. A random forest classifier based off top-ranked radiomic features as well as VAS scores were independently evaluated for predicting pathology-defined severe inflammation and fibrosis via ROC analysis.

Results: Two distinct sets of radiomic features capturing textural heterogeneity (patterns, local entropy) within strictures on MRE were significantly associated ($p<0.01$) with severe inflammation and severe fibrosis respectively; across both discovery (AUC=0.66 for inflammation, 0.76 for fibrosis) and hold-out validation (AUCs=0.71 for inflammation, 0.73 for fibrosis). By comparison, radiological global VAS had an AUC=0.68 for identifying severe inflammation and AUC=0.47 for identifying severe fibrosis. Combining radiomic features with VAS resulted in no significant improvement in predictive performance for either pathologic phenotype (validation AUC=0.71 for inflammation, 0.73 for fibrosis).

Conclusions: Radiomic analysis shows improved performance in identifying severe inflammation and severe fibrosis in CD strictures on MRE compared to radiological visual assessment scoring.

Clinical Relevance/Application: Objective evaluation of extent of fibrosis and inflammation in stricturing CD could enable more targeted treatment selection for this disease. Quantitative radiomics in conjunction with radiological evaluation could provide an avenue toward more accurate pathologic phenotyping of CD strictures via non-invasive MRE.

Example Use Case 2:

Purpose: 25% of patients with Crohn's disease (CD) develop severe stricturing disease which is non-responsive to standard-of-care medication. Early and non-invasive determination of the extent of inflammation and fibrosis within the stricture via CT enterography (CTE) could facilitate the selection of targeted therapy or earlier surgical resection to improve patient outcomes; but currently there is no validated and reliable approach for this differentiation. Results for machine-reader evaluation of severe inflammation and fibrosis in CD strictures via quantitative radiomic features and expert radiologist scoring of CTE are presented.

Methods and Materials: IRB approved, retrospective, single center study. 100 patients (n=66 for discovery; n=34 for hold-out validation) confirmed with stricturing CD on histopathology and CTE within 12 weeks of surgery. Histopathological Stenosis Therapy & Research (STAR) scoring of specimens (range 0-100, scores>50=severe) used as reference standard for inflammation and fibrosis each. An expert radiologist annotated the resected strictures on CTE and provided a global assessment of inflammation and Crohnic non inflammatory findings (fibrosis) using a 0-100 visual analog score (VAS). 1852 3D radiomic features were extracted from annotated strictures on CTE, from which the most relevant feature subsets were identified via cross-validated machine learning analysis in the discovery cohort for differentiating between (i) severe inflammation vs less severe, (ii) severe fibrosis vs less severe. Radiomic features and VAS scores were evaluated against pathology-defined severe inflammation and fibrosis in the validation cohort, via ROC analysis.

Results: Two distinct sets of radiomic features capturing textural heterogeneity (patterns, wavelets, local entropy) within strictures were significantly associated ($p<0.01$) with severe inflammation and severe fibrosis; across both discovery (AUC=0.69, 0.69) and hold-out validation (AUCs=0.72, 0.67). Radiological VAS had an AUC=0.64 for identifying severe inflammation and AUC=0.62 for identifying severe fibrosis.

Conclusions: Radiomic analysis shows improved performance in identifying severe inflammation and severe fibrosis in CD strictures on CTE compared to radiological visual assessment scoring.

Clinical Relevance/Application: Identifying degree of inflammation and fibrosis in CD strictures is critical for personalizing treatment pathways. Supplementing radiological visual assessment with quantitative radiomics could enable more accurate phenotyping of CD strictures potentially improving outcomes.

Therefore, in some embodiments the present disclosure relates to a non-transitory computer-readable medium storing computer-executable instructions that, when executed, cause a processor to perform operations. The operations include accessing an imaging data set having one or more radiological images of a patient having Crohn's disease, the one or more radiological images including one or more intestinal strictures; identifying a plurality of determinative features from within the one or more intestinal strictures in the one or more radiological images, the plurality of determinative features being associated with one or more pathological features used to identify inflammation or fibrosis within an intestinal stricture; and applying a machine learning model to the plurality of determinative features to identify an extent of inflammation or fibrosis within the one or more intestinal strictures.

In other embodiments, the present disclosure relates to a method of determining an extent of inflammation and/or fibrosis within an intestinal stricture. The method includes accessing an imaging data set having one or more radiological images of a patient having Crohn's disease, the one or more radiological images including an intestinal stricture; identifying a plurality of determinative features from within the intestinal stricture, the plurality of determinative features being associated with one or more pathological features used to identify inflammation or fibrosis; and applying a machine learning model to the plurality of determinative features to generate one or more of an inflammation score and a fibrosis score, the inflammation score having a first numeric value corresponding to an extent of inflammation within the intestinal stricture and the fibrosis score having a second numeric value corresponding to an extent of fibrosis within the intestinal stricture.

In yet other embodiments, the present disclosure relates to an apparatus configured to assess an extent of inflammation and/or fibrosis within an intestinal stricture. The apparatus includes a memory configured to store an imaging data set having one or more radiological images including an intestinal stricture; and a machine learning pipeline, including a radiomic feature extraction stage configured to extract a plurality of radiomic features from the intestinal stricture; a determinative feature identification stage configured to identify a plurality of determinative features from the plurality of radiomic features by associating one or more of the plurality of radiomic features with one or more pathological features used to identify inflammation or fibrosis within the intestinal stricture; and an inflammation and fibrosis model stage configured to apply one or more machine learning models to the plurality of determinative features to identify an extent of inflammation and fibrosis within the intestinal stricture.

Examples herein can include subject matter such as an apparatus, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2*d*. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:

accessing an imaging data set comprising one or more radiological images of a patient having Crohn's disease, wherein the one or more radiological images comprise one or more intestinal strictures;

extracting a plurality of radiomic features from within the one or more intestinal strictures in the one or more radiological images;

identifying a plurality of determinative features from the plurality of radiomic features by correlating one or more of the plurality of radiomic features with one or more pathological features used to identify inflammation and fibrosis within the one or more intestinal strictures;

providing the plurality of determinative features to a machine learning model trained to generate both an inflammation score and a fibrosis score based, at least in part, on the plurality of determinative features; and receiving, from the machine learning model, the inflammation score and the fibrosis score, wherein the inflammation score has a first numeric value corresponding to an extent of inflammation within the one or more intestinal strictures and the fibrosis score has a second numeric value corresponding to an extent of fibrosis within the one or more intestinal strictures.

2. The non-transitory computer-readable medium of claim 1, wherein the one or more pathological features comprise one or more features used in Stenosis Therapy and Research (STAR) scoring of the one or more intestinal strictures.

3. The non-transitory computer-readable medium of claim 1, further comprising:

identifying a plurality of determinative inflammation features from the plurality of radiomic features by correlating a first set of the plurality of radiomic features with a first set of the one or more pathological features used to identify the extent and severity of inflammation within the one or more intestinal strictures.

4. The non-transitory computer-readable medium of claim 1, further comprising:

determining a treatment plan for the patient based on the inflammation score and/or the fibrosis score.

5. The non-transitory computer-readable medium of claim 1, wherein the one or more radiological images comprise magnetic resonance enterography (MRE) images.

6. The non-transitory computer-readable medium of claim 5, wherein the plurality of determinative features comprise a first plurality of determinative inflammation features that are used to determine the extent of inflammation within the one or more intestinal strictures, the first plurality of determinative inflammation features comprising one or more of a median of a Law's feature, a Kurtosis of a Gabor feature, and a skewness of a Law's feature.

7. The non-transitory computer-readable medium of claim 5, wherein the plurality of determinative features comprise a first plurality of determinative fibrosis features that are used to determine the extent of fibrosis within the one or more intestinal strictures, the first plurality of determinative fibrosis features comprising one or more of a skewness of a Gabor feature, a skewness of a Law's feature, a kurtosis of a Law's feature, a kurtosis of a Gray mean feature, and a variance of a Gray range.

8. The non-transitory computer-readable medium of claim 1, wherein the one or more radiological images comprise computed tomography enterography (CTE) images.

9. The non-transitory computer-readable medium of claim 8, wherein the plurality of determinative features comprise a second plurality of determinative inflammation features that are used to determine the extent of inflammation within the one or more intestinal strictures, the second plurality of determinative inflammation features comprising one or more of a median of a Gradient Sobel feature, a skewness of a Law's feature, a variance of a Gradient Sobel feature, a kurtosis of a Gabor feature, a skewness of a Haralick energy feature, a skewness of a Law's feature, a median of a Gabor feature, and/or a median of a Law's feature.

10. The non-transitory computer-readable medium of claim 8, wherein the plurality of determinative features comprise a second plurality of determinative fibrosis features that are used to determine the extent of fibrosis within the one or more intestinal strictures, the second plurality of determinative fibrosis features comprising one or more of a skewness of a Law's feature, a median of a Gabor feature, a median of a Gray range feature, a median of a Haralick sum variance, a kurtosis of a Haralick energy feature, a median of a Law's feature, a median of a Gabor feature, and/or a variance of a Law's feature.

11. A method of determining an extent of inflammation and fibrosis within an intestinal stricture, comprising:

accessing an imaging data set comprising one or more radiological images of a patient having Crohn's disease, wherein the one or more radiological images comprise an intestinal stricture;

extracting a plurality of radiomic features from within the intestinal stricture;

identifying a plurality of determinative features from the plurality of radiomic features, wherein the plurality of determinative features are associated with one or more pathological features used to identify inflammation and fibrosis, wherein the plurality of determinative features are a subset of the plurality of radiomic features that differentiate between severe inflammation and minimal inflammation and between severe fibrosis and minimal fibrosis;

providing the plurality of determinative features to a machine learning model trained to generate both an inflammation score and a fibrosis score based, at least in part, on the plurality of determinative features; and receiving, from the machine learning model, the inflammation score and the fibrosis score, wherein the inflammation score has a first numeric value corresponding to the extent of inflammation within the intestinal stricture and the fibrosis score has a second numeric value corresponding to the extent of fibrosis within the intestinal stricture.

12. The method of claim 11, wherein the one or more radiological images comprise a magnetic resonance enterography (MRE) image or a computed tomography enterography (CTE) image.

13. The method of claim 11, wherein the plurality of radiomic features comprise texture features and morphological features.

14. An apparatus configured to assess an extent of inflammation and fibrosis within an intestinal stricture, comprising:

a memory configured to store an imaging data set comprising one or more radiological images comprising an intestinal stricture; and a machine learning pipeline, comprising:

a radiomic feature extraction stage configured to extract a plurality of radiomic features from the intestinal stricture;

a determinative feature identification stage configured to identify a plurality of determinative features from the plurality of radiomic features by associating one or more of the plurality of radiomic features with one or more pathological features used to identify inflammation and fibrosis within the intestinal stricture, wherein the plurality of determinative features are a subset of the plurality of radiomic features that differentiate between severe inflammation and minimal inflammation and between severe fibrosis and minimal fibrosis; and an inflammation and fibrosis model stage configured to apply one or more trained machine learning models to the plurality of determinative features to generate both an inflammation score and a fibrosis score, wherein the inflammation score has a first numeric value that is indicative of the extent of inflammation within the intestinal stricture and the fibrosis score has a second numeric value that is indicative of the extent of fibrosis within the intestinal stricture.

15. The apparatus of claim 14, wherein the one or more pathological features comprise one or more features used in Stenosis Therapy and Research (STAR) scoring of the intestinal stricture.

16. The apparatus of claim 14, wherein the plurality of radiomic features comprise one or more of texture features and morphological features.

17. The apparatus of claim 14, wherein the determinative feature identification stage is further configured to identify a plurality of determinative inflammation features from the plurality of radiomic features by correlating a first set of the plurality of radiomic features with a first set of the one or more pathological features used to identify inflammation; and wherein the inflammation and fibrosis model stage generates the inflammation score from the plurality of determinative inflammation features.

18. The apparatus of claim 14, wherein the determinative feature identification stage is further configured to identify a plurality of determinative fibrosis features from the plurality of radiomic features by correlating a first set of the plurality of radiomic features with a first set of the one or more pathological features used to identify fibrosis; and wherein the inflammation and fibrosis model stage generates the fibrosis score from the plurality of determinative fibrosis features.

19. The non-transitory computer-readable medium of claim 1, wherein the plurality of determinative features comprise a plurality of determinative fibrosis features that are used to determine the extent and severity of fibrosis within the one or more intestinal strictures and a plurality of determinative inflammation features that are used to determine the extent and severity of inflammation within the one or more intestinal strictures, wherein the machine learning model generates the inflammation score and a likelihood of severe inflammation based on the plurality of determinative inflammation features, wherein the machine learning model generates the fibrosis score and a likelihood of severe fibrosis based on the plurality of determinative fibrosis features.

20. The non-transitory computer-readable medium of claim 19, wherein the one or more radiological images comprise a magnetic resonance enterography (MRE) image and a computed tomography enterography (CTE) image, wherein the plurality of determinative features comprise a first plurality of determinative features extracted from the MRE image and a second plurality of determinative features extracted from the CTE image.

* * * * *